United States Patent
Gunn et al.

(10) Patent No.: US 6,986,783 B2
(45) Date of Patent: Jan. 17, 2006

(54) SYSTEM METHOD FOR REDUCING BRAIN INJURY PARTICULARLY IN NEWBORN INFANTS

(75) Inventors: Alistair Gunn, Auckland (NZ); Tania R. Gunn, deceased, late of Auckland (NZ); by Bernard Maurice Gunn, legal representative, Auckland (NZ); by Alistair Jan Gunn, legal representative, Auckland (NZ); by Derek Ivan Gunn, legal representative, Auckland (NZ); by Christopher Bernard Gunn, legal representative, Auckland (NZ); by Diana Katrina Coldham, legal representative, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 126 days.

(21) Appl. No.: 10/419,108

(22) Filed: Apr. 21, 2003

(65) Prior Publication Data

US 2003/0176902 A1 Sep. 18, 2003

Related U.S. Application Data

(63) Continuation of application No. 09/983,685, filed on Oct. 25, 2001, now abandoned, which is a continuation of application No. 09/445,607, filed on Sep. 21, 2000, now abandoned.

(30) Foreign Application Priority Data

Jun. 9, 1997  (NZ) ................................................ 328046
Jun. 9, 1998  (NZ) ................................ PCT/NZ98/00081

(51) Int. Cl.
*A61F 7/00* (2006.01)

(52) U.S. Cl. ........................ 607/110; 607/108; 607/109
(58) Field of Classification Search ................. 607/108, 607/109, 110; 600/21, 22
See application file for complete search history.

(56) References Cited

U.S. PATENT DOCUMENTS

| | | | | |
|---|---|---|---|---|
| 4,455,472 A | * | 6/1984 | Moss .......................... | 219/217 |
| 4,566,455 A | * | 1/1986 | Kramer ....................... | 607/109 |
| 4,809,677 A | | 3/1989 | Mackin et al. | |
| 4,920,963 A | | 5/1990 | Brader | |
| 4,987,896 A | | 1/1991 | Nakamatsu | |
| 5,241,959 A | * | 9/1993 | Kim et al. ................... | 607/104 |
| 5,261,399 A | | 11/1993 | Klatz et al. | |
| 5,269,369 A | | 12/1993 | Faghri | |
| 5,453,077 A | * | 9/1995 | Donnelly et al. ............. | 600/22 |
| 5,486,204 A | * | 1/1996 | Clifton ........................ | 607/96 |
| 5,603,728 A | | 2/1997 | Pachys | |
| 5,913,885 A | * | 6/1999 | Klatz et al. .................. | 607/104 |
| 6,128,795 A | | 10/2000 | Stanley et al. | |
| 6,185,744 B1 | * | 2/2001 | Poholski ........................ | 2/102 |
| 6,312,453 B1 | * | 11/2001 | Stefanile et al. ............ | 607/109 |
| 6,620,188 B1 | * | 9/2003 | Ginsburg et al. ........... | 607/106 |

* cited by examiner

*Primary Examiner*—Rosiland Rollins
(74) *Attorney, Agent, or Firm*—Nixon & Vanderhye

(57) ABSTRACT

A method for preventing or reducing the development of delayed brain damage in a patient, comprises applying headwear (1) to the patient's head and circulating a fluid coolant through conduits (3) or passages in the headwear to cool the brain and thermostatically controlling the coolant temperature within a predetermined range to maintain the brain at a temperature sufficiently below normal for an extended period sufficient to prevent the death of neurons, glial or other cells that would otherwise die as a consequence of direct injury to the brain or other injury to the patient likely to cause injury to the brain.

21 Claims, 4 Drawing Sheets

SYSTEM METHOD FOR REDUCING BRAIN INJURY PARTICULARLY IN NEWBORN INFANTS

This application is a continuation of application Ser. No. 09/983,685, filed Oct. 25, 2001, now abandoned which is a continuation of application Ser. No. 09/445,607, filed Sep. 21, 2000, now abandoned the entire content of which is hereby incorporated by reference in this application.

FIELD OF INVENTION

The invention comprises apparatus and a method for preventing or reducing delayed brain damage in a patient, and headwear for fitting to a patient's head for use with the apparatus and method of the invention.

BACKGROUND OF INVENTION

During brain injury, the brain is deprived of freshly oxygenated blood. Following this, neurons in the brain die soon after or at a later stage occurring hours to days after the insult and are not capable of regeneration. Glial cells, which are non-neuronal cells essential for normal brain functioning, also die. Permanent loss of function is a likely outcome of a severe injury to the brain.

Perinatal hypoxic-ischemic injury continues to be a major cause of death or later neurodevelopmental sequelae. This type of head injury in the neonate occurs during asphyxial, traumatic, toxic, infectious, metabolic, ischemic or hypoxic insults to the brain. Specifically, perinatal asphyxia caused by cord occlusion or associated with intrauterine growth retardation; perinatal asphyxia associated with failure of adequate resuscitation or respiration; near miss drowning, near miss cot death, carbon monoxide poisoning, ammonia or other gaseous intoxication, coma, hypoglycaemia and status epileptics; stroke; cerebral trauma. Experimental and clinical studies have shown that hypoxic ischemic encephalopathy (HIE) is an evolving process. Following the primary phase of energy failure during asphyxia cerebral metabolism may initially recover in a latent phase, but then deteriorate in a secondary phase of brain injury 6 to 15 hours later. In the human infant the severity of delayed energy failure after asphyxia is correlated with adverse neurodevelopmental outcome at one and four years of age.

It appears that hypothermic intervention in pathological processes occurring in the brain after brain injury may result in an improved neural outcome (Marion et al., New Eng. J. Med., 336:540–546 (1997)). Experimentally, hypothermic treatment following reperfusion after brain injury has been shown to increase numbers of viable neurons (Gunn et al., J. Clin, Invest, 99:248–256 (1997)).

Hypothermic therapy after brain injury is one method that can be used to rescue neurons and other cells from the phase of delayed brain damage that occurs after reperfusion. It involves cooling the brain tissue to a temperature of 30–34° C. As a consequence, pathological processes leading to delayed neuronal and other cell death are inhibited by as yet unknown mechanism/s.

The adverse consequences of hypothermia and the importance of maintaining newborn infants in the thermoneutral range have been known to pediatricians for the past 40 years, since the classic study by Silverman et al, in which infants 1501 g and more kept in "hypothermic" incubators had temperatures of 34.7±0.7° C. These findings were confirmed in subsequent studies with no cause for this increased mortality found at autopsy. It is thus important to limit the developing whole body cooling associated with cerebral hypothermia.

Cooling for hypothermic therapy is presently achieved by cold room technology involving a heat exchanger in heart-lung bypass surgery. This kind of surgery takes place in a room the size of a large commercial freezer. Major drawbacks with the cold room technology include that it is invasive and expensive, as a highly skilled team of medical personnel are necessary to operate a standard heart-lung bypass machine. Cooling can also be achieved by using natural or synthetic icepacks. These kinds of methods and devices have drawbacks. The disadvantages with natural and synthetic icepacks include melting, and the cooling temperature cannot be regulated.

U.S. Pat. No. 5,261,339 discloses a device and method for resuscitating the brain as a result of ischemic and anoxic injuries which comprises a head enveloping helmet and a neck supporting back plate with interconnected hollow cavities through which chilled gas form an activated coolant source or cooled liquids pass to chill the brain and upper spinal column. The device is intended for short-term use in the field at a trauma site on persons who have suffered cardiac arrest, respiratory arrest, stroke, suffocation, drowning or similar, to prevent neurologic injury from immediate lack of bloodflow to the brain, or oxygen to the brain, which may occur within minutes of cessation or substantial reduction of blood or oxygen flow.

SUMMARY OF INVENTION

The invention provides an apparatus and method particularly intended to prevent or reduce the development of delayed brain damage, or the secondary phase of brain damage. It has been found that neuronal rescue may be achieved by cooling the brain for an extended period of hours to days after injury while preferably also warming the general body to maintain and control the body temperature to limit systemic hypothermia.

In broad terms in one aspect the invention comprises apparatus for preventing or reducing the development of delayed brain damage in a patient, comprising:

headwear to be fitted to the patient's head and comprising conduits or passages within the headwear through which a fluid coolant may be circulated to cool the brain;

a reservoir to contain fluid coolant, cooling means to cool and maintain the fluid in the reservoir at a predetermined temperature, piping to connect the reservoir to the headwear, and means to circulate the fluid coolant from the reservoir to the patient headwear; and warming means arranged to maintain and control the temperature of the rest of the patient's body.

Preferably the coolant comprises a liquid coolant such as water, but other liquids or gases may be used. Preferably a liquid coolant such as water is recirculated back to the reservoir in a closed loop. In an alternative arrangement however, liquid $CO_2$ or similar stored under pressure in a cylinder connected to the headwear may be released so that gaseous $CO_2$ flows within the headwear as a cooling medium before being vented to the ambient environment via an outlet from the headwear.

The warming means may comprise an overhead heater directed to maintain and control the patient's general body temperature against the temperature reducing effect of the cooling of the brain or alternatively a heated mattress on which the patient lies. A heated mattress may comprise fluid conduits or passages through which warm water at a thermostatically controlled temperature is passed, an electrically heated mattress or pad, or a heated jacket which is worn by the patient or blanket which is placed over the patient.

Alternatively again, the warming means may comprise a cradle or cot incorporating heating elements in the walls and/or base of the cradle or cot to create a temperature controlled environment for the patient.

Very preferably the apparatus also comprises a control system arranged to thermostatically control the temperature of both the coolant circulating through the headwear to cool the patient's brain and warming means to maintain the patient's general body temperature, and the temperature differential such that the patient's body temperature is maintained in the range 35–37° C. and typically at 36.5–37° C. and the brain temperature is maintained in the range 30–34° C. and typically in the range 32–34° C.

In broad terms in a second aspect the invention comprises headwear for fitting to a patient's head, comprising a cap or bonnet formed of a soft, pliant material and comprising conduits or passages to circulate a coolant through the headwear to cool the brain.

Preferably the headwear comprises a fabric cap or bonnet comprising a removably fitted plastic cooling pad through which the coolant is arranged to circulate, which may be removed so that the bonnet and cooling pad may be laundered and sterilised separately. The cooling pad may be a lightweight plastic pad formed by heat welding together two plastic layers at selected intervals to create a pad having internal passages through which the coolant can circulate, and an inlet and outlet connection to connect the cooling pad to the fluid supply. It is also possible that the cap or bonnet itself may be formed by heat welding together layers of a synthetic material at selected points to form a cap or bonnet having integral fluid passages.

The outer layer forming the cap or bonnet may have an attractive colour and/or a pattern on its exterior, Alternatively and in one preferred form, the cooling pad is formed by soft plastic tubing woven to form a cooling pad and held together by external ties or similar, which is fitted in the cap or bonnet.

In broad terms in a third aspect the invention comprises a method for preventing or reducing the development of delayed brain damage in a patient, comprising applying headwear to the patient's head and circulating a fluid coolant through conduits or passages in the headwear to cool the brain to a temperature sufficiently below normal body temperature to rescue neurons, thermostatically controlling the coolant temperature to maintain the coolant temperature within a predetermined range for an exended period.

Preferably cooling is maintained for at least 12 hours and more preferably for 24–72 hours post-injury. It is believed that the secondary phase of brain damage may be prevented or minimised even if cooling is not commenced until up to 6 hours post-injury.

Preferably the brain is cooled to a temperature in the range 30–34° C. and most preferably in the range 32–34° C.

Preferably the method also includes warming the patient's general body to maintain general body temperature at about 36.5–37° C. and down to 35° C. if appropriate.

Preferably the method also includes monitoring a patient's brain and body temperatures and controlling the brain cooling and body warming to maintain both the head and body temperatures within predetermined ranges. There is a gradient of increasing temperature from the exterior of the patient's head to the centre of the brain. Brain temperature is preferably assessed and monitored via a nasopharyngeal temperature probe. We have found a nasopharyngeal temperature probe to be a reliable and conveniently used indicator of brain temperature. Brain temperature may be assessed by alternative means such as a temperature sensor in the auditory canal.

With the apparatus and method of the invention, it is believed that neurons and other cells in areas of the brain affected by injury that were destined to die during the period of delayed brain damage will be rescued. The patient recovers with increased chances of survival and decreased or no brain damage. By rescue is meant preventing the death of neurons, glial and other cells that would otherwise die as a consequence of brain injury. Such injury may arise due to asphyxia, ischemia, cardiac surgery, stroke, toxins, infections, trauma, haemorrhage, or surgical damage to the brain for example.

The apparatus and method of the invention are particularly but not exclusively suitable for treating brain injury or potential brain injury in newborn infants. In particular we have found that mild selective head cooling combined with mild systemic hypothermia in term newborn infants following perinatal asphyxia is a safe and convenient method of quickly reducing cerebral temperature, with an increased gradient between the surface of the scalp and the centre of the brain. The safety of mild hypothermia with selective head cooling is in contrast with the historical evidence of adverse effects with greater depths of whole body hypothermia.

BRIEF DESCRIPTION OF DRAWINGS

The invention will be further described with reference to the accompanying drawings, by way of example and without intending to be limiting. In the drawings.

DETAILED DESCRIPTION

The invention will be further described with reference to the prevention or reduction of brain damage in newborn(s) but it should be understood that the method and apparatus of the invention can also be used with children and adults. It may also be particularly suited for use in older patients as stroke and head injury cause increased brain temperature.

Figure 1:
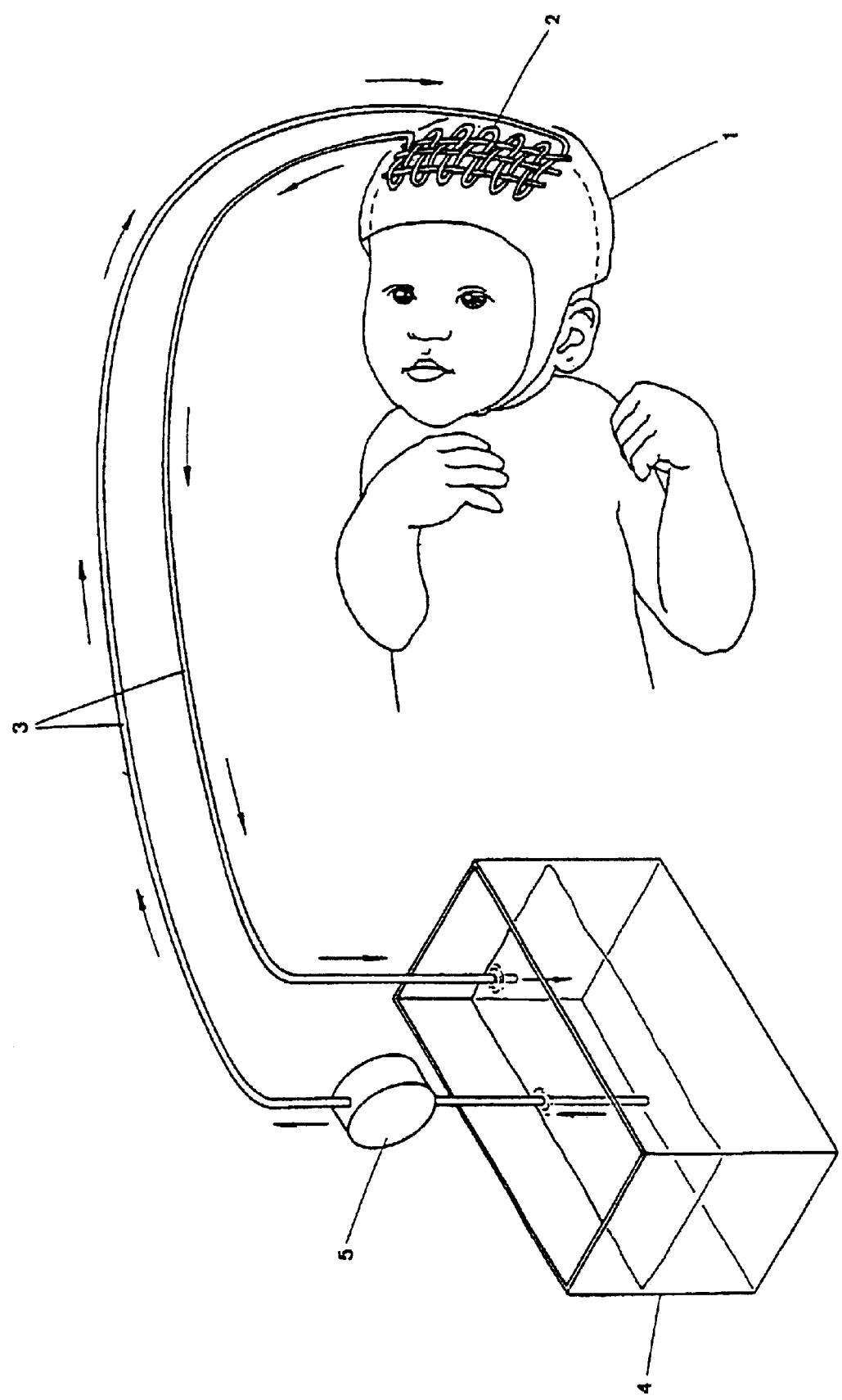
FIG. 1 shows an infant wearing headwear of the invention and schematically illustrates the operation of the apparatus and method of the invention.
Figure 2:
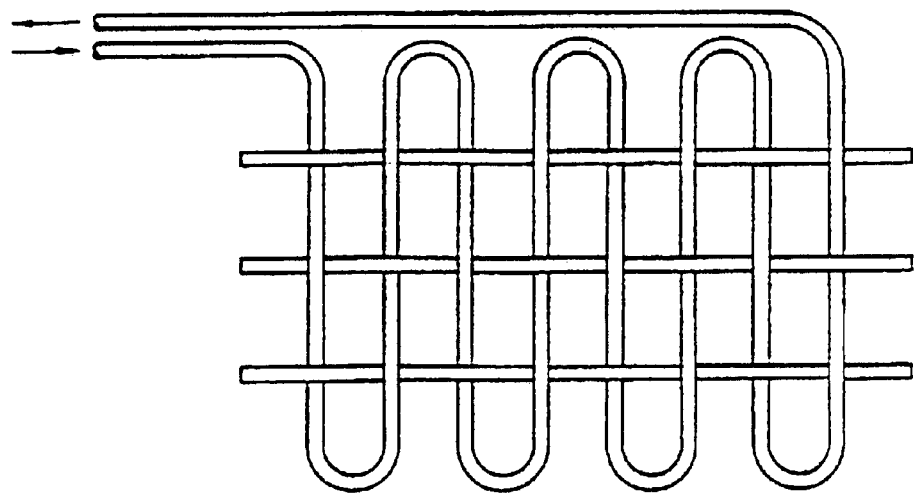
FIG. 2 shows in detail one form of cooling pad of headwear of the invention.

Referring to FIGS. 1 and 2, a cap or bonnet 1 is placed on the infant's head. The cap or bonnet is formed of a soft, pliant material and comprises conduits to circulate a coolant. In the preferred form shown the bonnet is formed from soft fabric material so that the bonnet has an attractive external appearance, and a cooling pad 2 shown in particular in FIG. 2 is fitted within the bonnet 1 so that the bonnet when tied beneath the chin of the infant will hold the cooling pad 2 against the infant's scalp.

Alternatively the bonnet may be secured beneath the chin by VELCRO or with an elastic head band secured by VELCRO around the head or by other suitable means. In the preferred form the cooling pad 2 is formed from soft, woven tubing as shown but alternatively the cooling pad may be formed by heat welding two plastic layers together to form passages through such a cooling pad for example.

The cooling pad may be retained within a pocket in the cap or bonnet which is closed by a VELCRO strip or similar, so that the cooling pad is removable from the bonnet to enable the bonnet to be laundered and the cooling pad to be separately sterilised. Alternatively, the cooling pad may be formed as a low cost item so that it can be disposed of after use. Alternatively again, the cooling pad may be retained within the bonnet by ties or may similarly be intended to be placed against an infant's head with the bonnet then being placed on the infant's head over the cooling pad to retain the cooling pad in place. Further alternatively an entire cap or bonnet may be formed by heat welding two appropriately shaped plastic or synthetic layers of material together to form a bonnet with integral passages for the flow of cooling fluid.

The bonnet 2 is connected by tubing 3 to a reservoir 4 of fluid coolant such as water. An associated cooling or refrigeration system maintains the water in the reservoir 4 at a predetermined temperature, such that when the water is circulated through the cooling pad 2 in the bonnet the infant's brain temperature will be reduced to preferably 30–34° C. as measured via a nasopharyngeal probe. A pump S is arranged to circulate the fluid.

Figure 3:
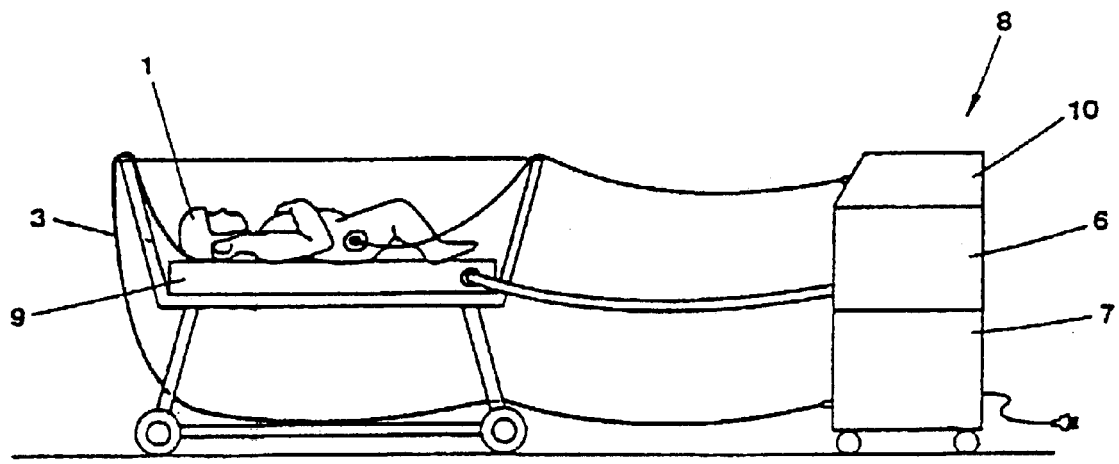
FIG. 3 diagrammatically shows one form of apparatus of the invention comprising a mattress in which heated water is circulated to maintain the patient's general body temperature.
Figure 4:
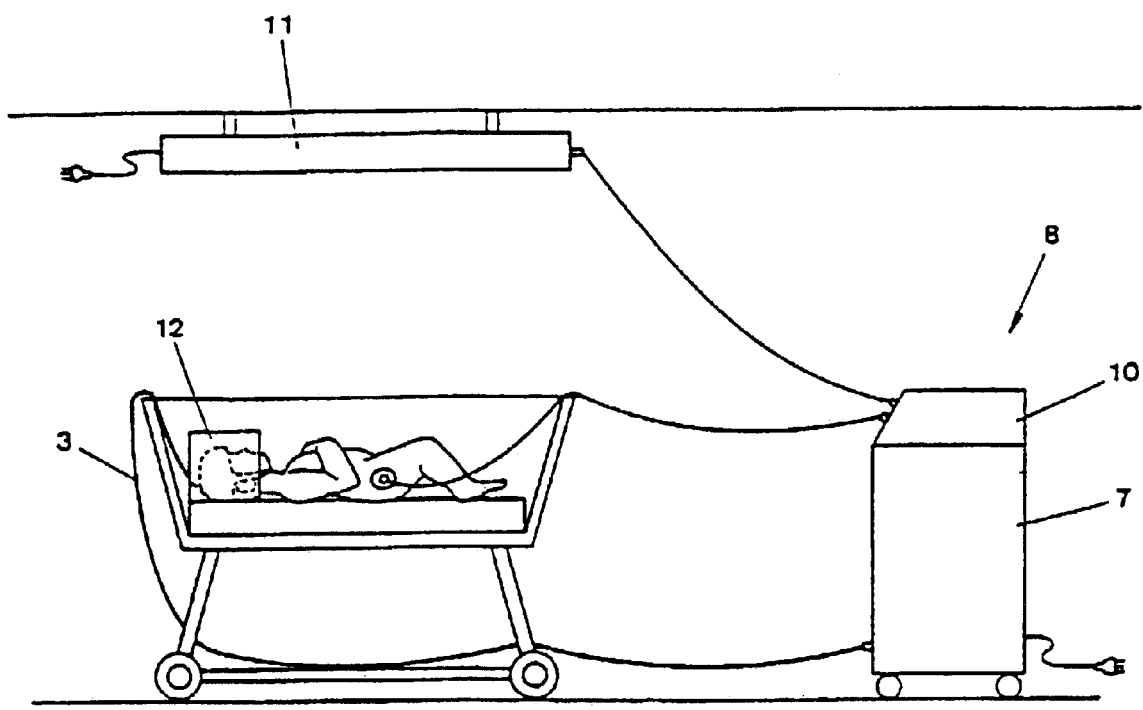
FIG. 4 diagrammatically shows another form of apparatus of the invention comprising an overhead heater used to maintain the patient's general body temperature.
Figure 5:
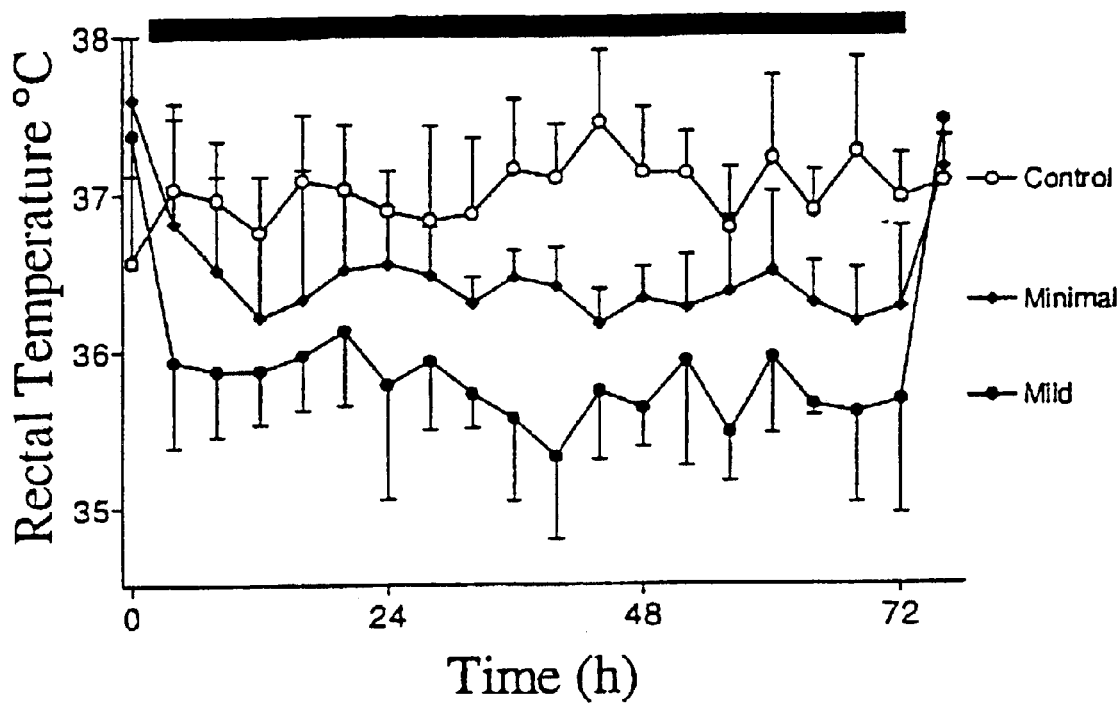
FIG. 5 graphically shows changes in rectal temperature in asphyxiated infants starting from the time of enrolment in a study described subsequently, in control (O, n=10), minimally cooled (♦, n=6) and mildly cooled infants (●, n=6). The period of cooling is shown by the solid bar. Cooling (or routine monitoring for controls) were stopped between 48 and 72 h in three control, two minimal and four mild infants; one control infant died in the first 24 h. The mildly cooled group showed a significant reduction in rectal temperature ($p<0.01$) during the cooling phase. Mean±SD.

Referring to FIGS. 3 and 4, the preferred form of the apparatus also comprises warming means arranged to maintain the rest of the patient's body at or close to normal body temperature range. Referring to FIG. 3, a unit 6 which may be on casters so that it may be conveniently moved around in a hospital houses the reservoir and refrigeration means at 7 and a pump connected to the headwear, and also at 8 a second reservoir and pump which are connected to a mattress 9 in the base of the cradle or cot. The unit also houses an associated water heater to heat the second reservoir. The mattress 9 or part of the mattress comprising the passages in which warm water is circulated does not extend beneath the infant's head.

A thermostatic control system 10 controls the cooling or refrigeration system which maintains the temperature of the cooling fluid in the reservoir 4 and the heater which maintains the temperature of the warm water in the reservoir 7. A sensor or probe indicating brain temperature such as a nasopharyngeal probe is connected to the control system 10, and a sensor or probe indicating general body temperature is also connected to the control system, such as one or more temperature sensors or probes attached to the infant's body. The control system controls the temperature of both the cooling and warning fluids to maintain them, and the temperature differential between the infant's nasopharyngeal and general body temperatures, within closely controlled ranges.

In the apparatus of FIG. 4 maintenance of the infant's general body temperature is by an overhead heater 11 which may not be connected to the control system 10 but having an output chosen to generally maintain an infant's body temperature at the appropriate level, or which may also be thermostatically controlled by the control system 10. In this case to prevent the heater from also raising the patient's head temperature, a cover or "shield" 12 of heat reflective material is placed within the cradle or cot to extend generally over the patient's head. Such a cover or similar may have a heat reflective exterior formed of silver foil for example.

With the method and apparatus of the invention, treatment may be carried out to prevent or reduce secondary brain damage ie to improve neural outcome being a state of neural competence occurring after, or as a consequence of natural repair processes, without resultant systemic hypothermia. The apparatus of the invention may be configured as shown in FIGS. 3 and 4 so as to be used in sterile conditions such as neonatal intensive care units for example.

EXPERIMENTAL & TRAILS

The following describes experimental work carried out using the method of the invention:

Term infants $\geq 37$ weeks considered to be at high risk following perinatal asphyxia were admitted to the Neonatal Intensive Care Units at National Womens Hospital, Auckland, New Zealand, after labor and delivery. The inclusion criteria were an umbilical arterial pH $\leq 7.09$ or Apgar scores $\leq 6$ at 5 minutes plus encephalopathy consisting of lethargy/stupor, hypotonia, abnormal reflexes including an absent or weak suck. The infants were evaluated 2–5 hours after birth; the infants were randomised by sequential computer generated numbers to either a control group with a rectal temperature maintained from 37.2–36.8° C., or to one of two cooling groups. A minimal systemic hypothermia group was studied with allocated rectal temperature 36.5–36.0° C. (n=6). A mild hypothermic group was studied with rectal temperature 35.9–35.5° C. (n=6). Overhead heaters servo-controlled to the abdominal skin were adjusted to maintain the allocated rectal temperature. Head cooling was accomplished by a cooling cap consisting of Silclear tubing (Degania Silicone, Degania Bet, Israel) coiled to fit around the scalp of the infants and held in place by a baby bonnet. Water cooled to 10° C. by a small thermostatically controlled cooling unit was circulated through the coil by a water pump. The infants were cooled for 72 h, however cooling was discontinued between 48 and 72 hours if the infant recovered neurologically (3 control infants, 2 infants in the minimal group, and 4 in the mild group). The rectal, fontanelle and nasopharyngeal temperatures were continuously monitored with thermistors (IncuTempl, Mallinckrodt Medical, St Louis, Mo.). All infants had continuous electrocardiograph and pulse oximetry monitoring and umbilical arterial catheters for blood gas and blood pressure monitoring as indicated clinically.

The medical charts of the mothers were reviewed and the information collected included complications of pregnancy induced hypertension and diabetes, labor complications such as cord prolapse, uterine rupture, vasa previa, dystocia or abruption of the placenta and fetal heart rate decelerations.

Figure 6:
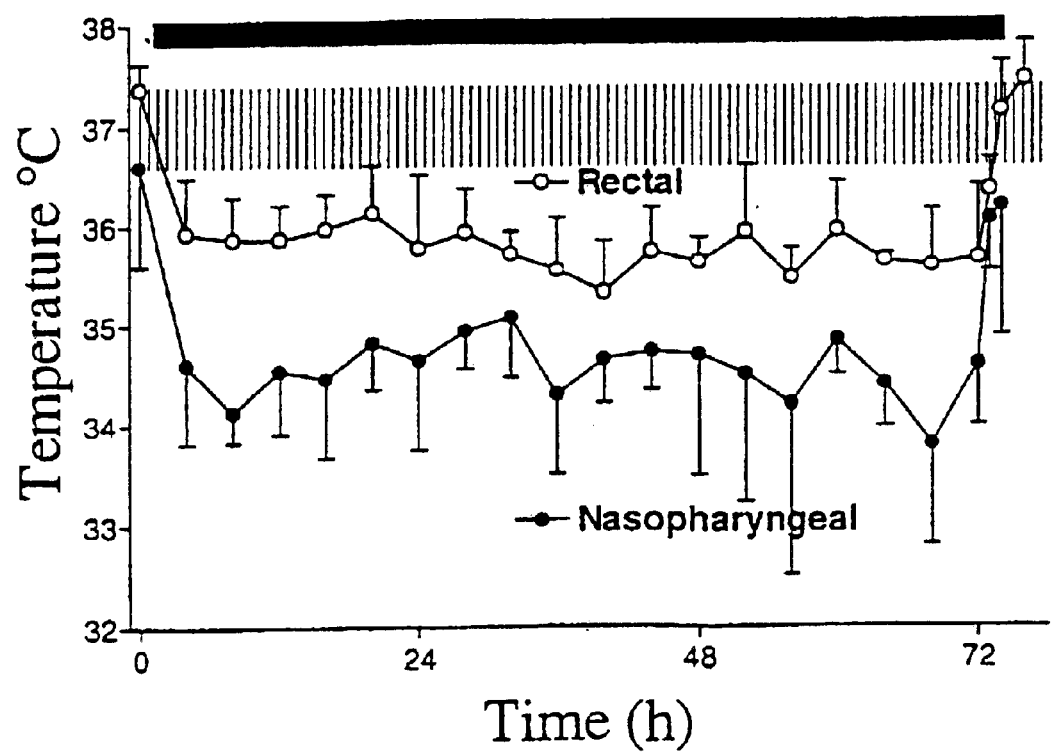
FIG. 6 graphically shows changes in rectal and nasopharyngeal temperature in the mild systemic hypothermia group. The period of cooling is shown by the solid bar. The shaded region shows the normal range for rectal temperature (36.6 to 37.4° C.). There is a significant ($p<0.05$) increase in the temperature difference between these two sites during the period of cerebral cooling, compared with the baseline measurements or the recovery phase. Mean±SD.

The rectal temperatures for the 3 groups of infants are shown in FIG. 1. The rectal temperatures at the time of enrolment were 36.6±1.4 (range 34.5 to 38.2) for the control group, 37.6±0.4 (37.1 to 38.1) for the minimal group and 37.4±0.3 (37.1 to 38.1) for the mild group. The mean temperature during the study period for the control infants was 37.0±0.2° C., for minimal cooling 36.3±0.2° C. and for those in the mild cooling group 35.7±0.2° C. during the cooling period. For the infants allocated to the mild cooling group, the mean rectal temperature compared to the nasopharyngeal temperature is shown in FIG. 6. The nasopharyngeal temperature of 34.5±0.3° C. was 1.2° C. lower than the rectal temperature during cooling and 0.5° C. lower when cooling had ceased.

The scalp (fontanelle) temperature consistently fell to around 28° C. during mild cooling, provided close contact was maintained between the cooling cap and the scalp. Although intracerebral measurements were not performed, nasopharyngeal temperature is an alternative which is commonly used during hypothermic cardiopulmonary bypass surgery in infants, and adults. Changes in nasopharyngeal temperature correlate well with jugular venous and/or intracerebral temperatures although measurements may lag behind during rewarming, and potentially may be affected by the temperature of ventilatory gases. The relationship of nasopharyngeal and parietal cortical temperature, and the efficacy of external head cooling has been demonstrated in a study of adult swine, where local application of icepacks to the head and neck after cardiac arrest reduced nasopharyngeal (−2.9±1.4° C.), parietal cortex (−2.1±0.6° C.) and esophageal (−1.4±0.8° C.) temperatures in 20 min. In the present study, the nasopharyngeal temperature was a mean of 1.2° C. below the rectal temperature during mild cooling compared to just 0.5° without cooling.

Following discharge the infants had a neurodevelopmental assessment in the follow-up clinic by the paediatrician at 3, 6 and 12 months. In addition, at 18-months, they are being assessed by a developmental psychologist using the Bayley Seale; this is still in progress. Incidences were compared by Fisher's Exact Test. The groups were compared by two way Mann Whitney U test.

In conclusion, selective head cooling preferably also combined with mild systemic hypothermia in term newborn infants following perinatal asphyxia is a practical method of quickly reducing cerebral temperature, with an increased gradient between the surface of the scalp and core temperature. This approach may allow the adverse effects of systemic hypothermia to be minimised.

The foregoing describes the invention including preferred forms thereof. Alterations and modifications as will be obvious to those skilled in the art are intended to be incorporated in the scope hereof.

What is claimed is:

1. A method for preventing or reducing the development of delayed brain damage in a newborn infant, comprising applying headwear to the infant's head and circulating a fluid coolant through conduits or passages in the headwear to cool the brain of the infant and thermostatically controlling the coolant temperature within a predetermined range to maintain the infant's brain at a temperature sufficiently below normal for an extended period sufficient to prevent the death of neurons, glial or other cells that would otherwise die as a consequence of direct injury to the brain or other injury to the infant likely to cause injury to the brain, while simultaneously warming the rest of the infant's body, and monitoring both the infant's head and body temperatures and thermostatically controlling the brain cooling and body warming to maintain both the head and body temperatures.

2. A method according to claim 1 including maintaining said cooling and warming for at least 12 hours after injury to the infant.

3. A method according to claim 1 including maintaining said cooling and warming for at least 24 hours after injury to the infant.

4. A method according to claim 1 including maintaining said cooling and warming for between 12 and 72 hours after injury to the infant.

5. A method according to claim 1 wherein said cooling maintains the infant's brain at a temperature in the range 30–34° C.

6. A method according to claim 5 wherein said cooling maintains the infant's brain at a temperature in the range 32–34° C.

7. A method according to claim 5 including warming the infant's general body to maintain the infant's general body temperature in the range 35–37° C.

8. A method according to claim 6 including warming the infant's general body to maintain the infant's general body temperature in the range 35–36° C.

9. A method according to claim 1 wherein the head temperature is monitored by a sensor attached to the scalp of the infant.

10. A method according to claim 1 including carrying out the cooling and warming to cause a temperature difference between the infant's brain and general body of at least 0.5° C.

11. A method according to claim 1 including carrying out the cooling and warming to cause a temperature difference between the infant's brain and general body of at least 1° C.

12. Apparatus for preventing or reducing the development of delayed brain damage in a newborn infant, comprising:
    headwear to be fitted to the infant's head and comprising conduits or passages within the headwear through which a fluid coolant may be circulated to cool the brain of the infant;
    a reservoir to contain fluid coolant, cooling means to cool and maintain the fluid in the reservoir at a predetermined temperature, piping to connect the reservoir to the headwear, and means to circulate a fluid coolant from the reservoir to the infant headwear;
    warming means arranged to warm the rest of the infant's body, and
    a control system arranged to thermostatically control the temperature of both the coolant circulating through the headwear to cool the infant's brain and warming means to maintain the infant's general body temperature.

13. Apparatus accordin to claim 12, wherein the control system is arranged to control the cooling means and warming means to maintain the infant's brain temperature in the range 30–34° C. and the patient's general body temperature in the range 35–37° C.

14. Apparatus according to claim 13 wherein the control system is arranged to control the warming means to maintain the infant's general body temperature in the range 35–36° C.

15. Apparatus according to claim 12 wherein the warming means comprises an overhead heater.

16. Apparatus according to claim 12 wherein the warming means comprises a heated mattress on which the infant lies.

17. Apparatus according to claim 12 wherein the warming means comprises a heated pad on a mattress.

18. Apparatus according to claim 12 wherein the warming means comprises a heated jacket which is worn by the infant or blanket which is placed over the infant.

19. Apparatus according to claim 12 wherein the warming means comprises a cradle or cot incorporating heating elements in the walls, base, or walls and base of the cradle or cot to create a temperature controlled environment for the infant.

20. Apparatus according to claim 12 wherein the coolant is a liquid which is recirculated back to the reservoir in a closed loop.

21. Apparatus according to claim 12 comprising a mobile unit for use in a hospital, said unit comprising the cooling means and reservoir for fluid coolant, and the thermostatic control system for controlling the cooling means and the warming means.

* * * * *